United States Patent
Artley

(10) Patent No.: US 7,893,313 B2
(45) Date of Patent: Feb. 22, 2011

(54) REUSABLE INCONTINENCE PRODUCT WITH INSOLUBILIZED POLYETHYLENE GLYCOL AND DMDHEU

(76) Inventor: John W. Artley, 4 Park Ave., Apt. 10-R, New York, NY (US) 10016

( * ) Notice: Subject to any disclaimer, the term of this patent is extended or adjusted under 35 U.S.C. 154(b) by 0 days.

(21) Appl. No.: 11/058,737

(22) Filed: Feb. 15, 2005

(65) Prior Publication Data

US 2005/0234420 A1    Oct. 20, 2005

Related U.S. Application Data

(63) Continuation-in-part of application No. 10/022,959, filed on Dec. 18, 2001, now Pat. No. 7,264,638, and a continuation-in-part of application No. 11/005,083, filed on Dec. 6, 2004, now Pat. No. 7,585,330.

(60) Provisional application No. 60/551,823, filed on Mar. 10, 2004.

(51) Int. Cl.
*A61F 13/15* (2006.01)
*A61F 13/20* (2006.01)

(52) U.S. Cl. ...................... 604/360; 442/123

(58) Field of Classification Search ............. 604/367, 604/372–373, 358, 365, 360; 442/43, 46, 442/118, 119, 123, 153, 156, 164, 218, 301, 442/359, 360
See application file for complete search history.

(56) References Cited

U.S. PATENT DOCUMENTS

| | | | | |
|---|---|---|---|---|
| 2,583,553 A * | 1/1952 | Faure | ............ | 604/397 |
| 2,815,260 A * | 12/1957 | Melander | ............ | 8/137 |
| 3,759,261 A * | 9/1973 | Wang | ............ | 604/361 |
| 3,939,836 A * | 2/1976 | Tunc | ............ | 604/364 |
| 4,396,391 A * | 8/1983 | North | ............ | 8/181 |
| 4,585,450 A * | 4/1986 | Rosch et al. | ............ | 604/390 |
| 4,713,068 A * | 12/1987 | Wang et al. | ............ | 604/366 |
| 4,758,239 A * | 7/1988 | Yeo et al. | ............ | 604/366 |
| 4,818,600 A * | 4/1989 | Braun et al. | ............ | 442/76 |
| 4,908,238 A * | 3/1990 | Vigo et al. | ............ | 427/389 |
| 5,207,663 A * | 5/1993 | McQueen | ............ | 604/385.05 |
| 5,700,254 A * | 12/1997 | McDowall et al. | ............ | 604/378 |
| D412,574 S * | 8/1999 | Trombetta et al. | ............ | D24/124 |
| 6,287,581 B1 * | 9/2001 | Krzysik et al. | ............ | 424/402 |
| 6,521,087 B2 * | 2/2003 | Hansen et al. | ............ | 162/173 |
| 6,855,422 B2 * | 2/2005 | Magill et al. | ............ | 428/373 |
| 6,971,935 B1 * | 12/2005 | Gilmer | ............ | 441/106 |
| 2002/0120242 A1 * | 8/2002 | Tyrrell et al. | ............ | 604/364 |

* cited by examiner

*Primary Examiner*—Melanie J Hand
(74) *Attorney, Agent, or Firm*—Schmid PA

(57) ABSTRACT

Disclosed is a reusable incontinence products treated with a polyethylene glycol formulation in the form of a pad that is worn by a user for the control and collection of bodily fluids. The pad may include two or more layers, wherein one layer absorbs the bodily fluid and the other layer acts as a barrier layer to prevent the fluid from soiling a user's garments. Further embodiments are disclosed including a folder for conveniently carrying a supply of fresh pads and a waterproof pocket to contain soiled pads, and a pant for holding the pads in place next to the skin.

8 Claims, 4 Drawing Sheets

The Pant

The Folder

The Pant

REUSABLE INCONTINENCE PRODUCT WITH INSOLUBILIZED POLYETHYLENE GLYCOL AND DMDHEU

RELATED APPLICATION

This application claims priority to U.S. Provisional Patent Application Ser. No. 60/551,823, filed Mar. 10, 2004, and is a continuation-in-part of U.S. patent application Ser. No. 10/022,959, filed Dec. 18, 2001 now U.S. Pat. No. 7,264,638, and Ser. No. 11/005,083, filed Dec. 6, 2004 now U.S. Pat. No. 7,585,330, the contents of which are hereby incorporated in their entirety.

FIELD OF THE INVENTION

The present invention generally relates to incontinence products and to a greater degree the invention relates to reusable incontinence products treated with a polyethylene glycol formulation.

BACKGROUND

As the population continues to age an increasingly large number of these adults will suffer from age, stress, systemic, or surgically induced full or partial loss of bladder control. In the medical community, this condition is normally called "incontinence."

Numerous types of products—usually made from various woven or nonwoven materials—designed to help absorb and contain the urine after a loss of control episode (called an "insult") are widely available in commerce from many different manufacturers. Such types of incontinence products include: underpads to be placed beneath a bedridden patient; seat pads for wheelchair use; adult and infant diapers; various types of pants with built-in absorbent pads; and small shields or insert pads of a type used by ambulatory, light-incontinent patients. Typically shields and pads are placed inside an undergarment and positioned next to the skin.

Incontinence products are produced in both durable (meaning they can be washed and reused numerous times before throwing away) and disposable forms (meaning after a single use they must be thrown away).

Durable incontinence products are generally made from various woven fabrics, such as cotton, usually placed in several layers between a fluid barrier and a woven top cover such as birds-eye cotton. Because they incorporate woven-type fabrics they may be washed multiple times before wearing out, and having to be thrown away. However these types of products generally suffer from a lack of liquid holding capacity, may be expensive, can bunch up causing pressure points against the skin, or often leak causing discomfort for the user and soiling of the bed linens.

Disposable incontinence products are manufactured from many types of materials, and usually incorporate some form of fluid barrier to the outside. The absorbent materials used can include, for example, stacked sheets of newsprint paper, or tissue. Other types of materials used to make disposable incontinence products include various blends of fibers (for example, a 50/50 blend of cotton and polyester) formed into an entangled nonwoven web/matrix structure. These nonwoven structures may be made from one, or several, types of available production methods such as air laid, spunbond, needlepunched or hydroentangled. Whatever the form of nonwoven construction used, later, with dies or other forming techniques, these structures may be stamped, cut, bonded, sewn and/or shaped into various incontinence products.

Many of the disposable incontinence products available today incorporate a superabsorbent powder (SAP) made of polyacrylic acid, or starch, placed in the core of the structure to assist with capturing and holding the liquid after an insult. Generally in a powder or pellet form, the SAP, or starch, is inserted, or simply sprinkled, into, or onto, the substrate during conversion into an incontinence product. This is necessary, for without these chemistries disposable incontinence products generally do not hold liquids in sufficient quantities to be useful, or they leak, rendering the product unusable.

However there are several problems with the use of a SAP, or starch, in disposable incontinence products. For one, these chemicals are tenacious, and aggressively hold liquids in a gel-like state that will not easily give up liquid after an insult. Because of this, when the resulting product is disposed of in a landfill it may for many years maintain the liquid in its gel-state possibly causing the accidental spread of bacteria, odors, or result in downstream environmental problems. And because of the natural affinity of SAPs and starches to water, these types of incontinence products are inherently disposable as they cannot be washed and reused.

An additional problem with the incorporation of super absorbent chemistries into an incontinence products is when saturated with fluid (such as after an insult), the powders or pellets (now a gel) will swell in an irregular fashion, causing lumps to form within the structure. In some cases this may result in simple irritation and discomfort for the user. In other instances it may lead to pressure being applied to the skin in a manner that can result in the formation of lesions, or entryways, allowing the passage of dangerous bacteria into, or through, the epidermis causing infection and other health-related difficulties.

A further problem with disposable-type incontinence products is there is currently no satisfactory way for an ambulatory light-incontinent patient, for example, to readily carry a supply of unused shields or insert pads, nor is there a convenient way to carry ones that have been soiled for later disposal. Additionally, with currently available incontinent products there is often a concern by the user that when in a public place others may detect the odor of an insult, or can physically see, because of bulkiness, or even tell from hearing the rustle of paper or fabrics, that the patient is wearing a form of incontinence product.

Although these problems apply to both men and women, men generally do not benefit from the availability of shields and insert pads designed especially for their needs, or they are forced to rely on the use of disposable shields or pads designed originally as feminine hygiene products. Correspondingly men often suffer discomfort and embarrassment from having to use such products, and rather than enjoying a useful, productive life, these types of incontinent individuals will not venture from their residences.

And last, disposable insert shields and pads of the types now generally available are expensive, and for individuals on a limited budget, the cost of replacing these disposable products numerous times during a single day may pose an unnecessary financial burden. Recognizing that the currently available durable and disposable incontinence products, especially shields and insert pads for light incontinence, are inherently defective and offer numerous opportunities for improvement, the invention embodied herein provides the individual who is incontinent with a more comfortable, efficient, better performing, lower cost solution to the control of liquids than he, or she, is now able to acquire, while providing improved personal dignity and a better quality of life.

SUMMARY

The present invention provides for a reusable incontinent product in the form of a pad that is worn by a user for the control and collection of bodily fluids. The pad may include two or more layers, wherein one layer absorbs the bodily fluid and the other layer acts as a waterproof barrier layer to prevent any residual the fluid from seeping through the pad. The pad is worn next to the skin of a user, with the absorbent layer next to the skin and the barrier layer backing the absorbent layer to prevent the fluids from soiling the garments of the user. In a further embodiment, the present invention includes a folder for conveniently carrying a supply of fresh pads and storing soiled pads, and a pant for holding the pad in place on the user.

In greater detail, the reusable incontinent product or pad comprises an absorbent layer including a substrate treated with a hydrophilic polyethylene glycol formulation and a barrier layer. Additional layers are contemplated and may be used in the product. Furthermore, the absorbent layer and the barrier layer may comprise multiple layers. The substrate of the absorbent layer may include any nonwoven material such as felt or a hydroentangled structure. The barrier layer may be a polymeric sheet or a fabric material coated with a polymeric layer. The barrier layer may also be a coating applied to the absorbent layer.

Additionally, the substrate may exhibit various desirable characteristics. For example, the treated substrate may exhibit antimicrobial properties whereby the treated pad prevents populations of bacteria from growing. The antimicrobial properties of the treated substrate also provide protection from common odor-causing bacteria. The treated substrate also exhibits thermal buffering properties whereby heat can be absorbed or released to provide comfort to the user. Additionally, the product may further include a wear indicator. The wear indicator can be a colored patch, or ink applied directly, that fades as the pad is washed to reveal a different color thereby indicating the need to discard the product.

The hydrophilic polyethylene glycol formulation used to treat the substrate may comprise on a percent basis of the formulation between about 30% to about 60% polyethylene glycol, between about 10% to about 30% DMDHEU and between about 3% to about 10% of an acid. The polyethylene glycol may have a molecular weight between about 1200 and 1500.

A further embodiment includes a sealable folder for receiving a reusable incontinent product. The folder provides for a storage area to carry a supply of fresh pads including ones treated with a hydrophilic polyethylene glycol formulation. The folder also incorporates a waterproof pouch, or pocket, to receive used or soiled pads. The folder may also hold a pant for holding the pad in position next to the user's skin.

An additional embodiment includes a method of making a reusable incontinent product. The method includes providing an absorbent layer including a substrate treated with a hydrophilic polyethylene glycol formulation and a barrier layer that can be attached to the absorbent layer. The step of treating the substrate includes curing the treated substrate to a surface temperature of the substrate between about 200° F. to about 240° F. and then neutralizing the treated substrate.

DRAWINGS

DETAILED DESCRIPTION

Disclosed in greater detail is a reusable incontinent product having multiple layers for collecting bodily fluids of a user. The product may be in the form of a pad having two or more layers, wherein one layer absorbs the bodily fluid and the other layer acts as a waterproof barrier layer to prevent any residual fluid from fully seeping through the absorbent layer. The pad is configured such that the absorbent layer resides next to the skin of the user and the barrier layer backs the absorbent layer to prevent the fluids from soiling the garments of the user. Further embodiments are also disclosed including a sealable folder to be used for conveniently carrying a supply of fresh pads and receiving and holding used or soiled pads, a pant for holding the pad in place against the skin, and a method of making the reusable incontinent product.

Referring now in greater detail to the drawings in which like numerals indicate like parts throughout the several views, FIGS. 1-4 depict the reusable incontinent product and kit in various embodiments of the present invention.

The Product

Figure 1:
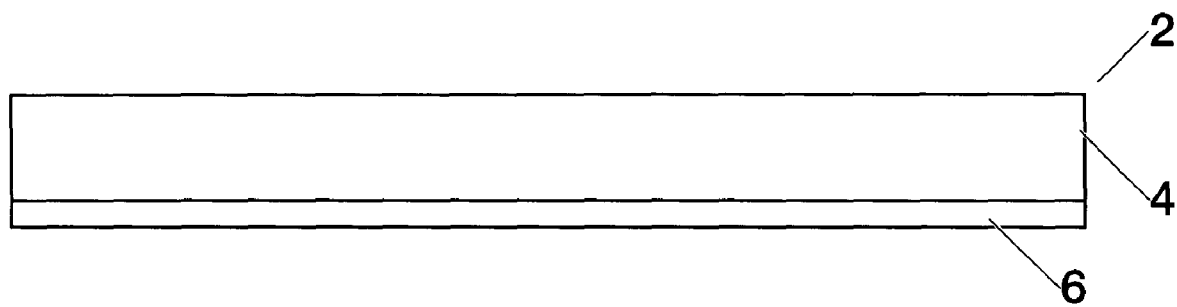
FIG. 1 illustrates a side view of the reusable incontinent product showing the absorbent layer and the barrier layer.

As illustrated in FIG. 1, the reusable incontinent product or pad 2 may comprise at least two layers. The term "product" may be used interchangeably with the term "pad". A first layer includes an absorbent layer 4 having a substrate treated with a hydrophilic polyethylene glycol formulation and a barrier layer 6. The substrate of the absorbent layer 4 may be formed of fibers, which have been previously treated with the hydrophilic polyethylene glycol formulation and then formed into the substrate. Additionally, further layers may be added to the product 2 and the additional layers may reside between the absorbent layer 4 and the barrier layer 6. Furthermore, the barrier layer 6 may be directly applied to the absorbent layer 4.

The product 2 includes in one embodiment the treated substrate 4 and barrier layer 6 joined together to form the product 2. The product 2 may be formed by cutting, punching, heating or any other method, into an absorbent shield or insert pad, or any other pad, of a shape and size allowing it to be positioned, and used, next to the skin in an area of the body suitable for capturing urine, or blood, or any other liquid discharged, or emitted, by the wearer.

In greater detail, the treated substrate comprising the absorbent layer 4 includes any woven or nonwoven fabric or material made from any fiber or blend of fibers, of any type of construction, that has been modified with the formulation and which formulation has been made insoluble and linked, or permanently bonded, to the material. The barrier layer 6 includes any water repellent or resistant substrate or coating, including films or topical solutions which may be operatively positioned such that a liquid may not flow through and out of the treated substrate. In one embodiment, the barrier layer 6 may be attached to or bounded to the treated substrate 4. The barrier layer 6 may be attached using glue, heat, by spray application, ultrasound, or any other method of joining by which fluids are prevented from soaking through the treated substrate 4, to soil or wet a garment, or piece of furniture or any object not usually found in a wet condition.

The Folder

Figure 2:
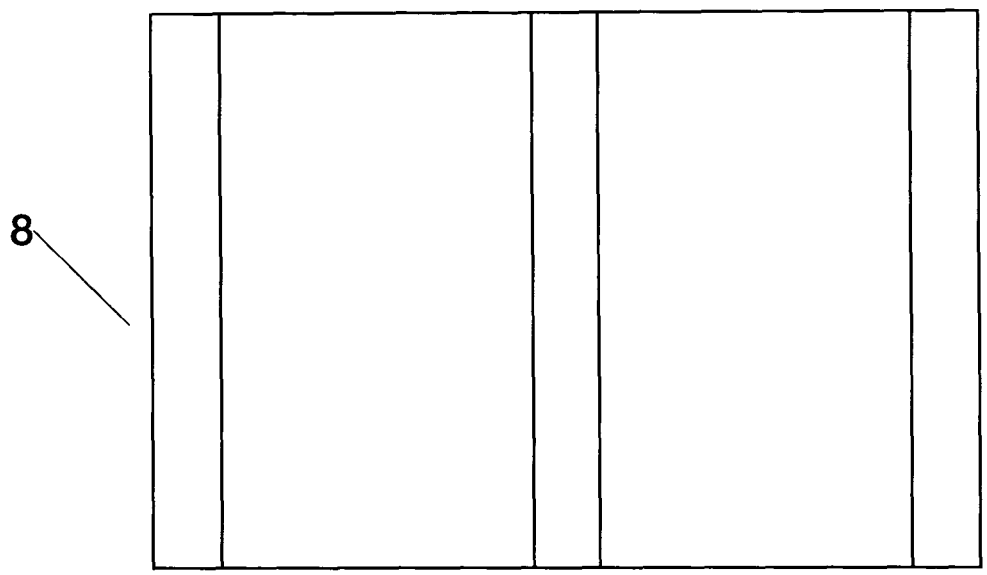
FIG. 2 depicts an embodiment of the folder in cooperation with the reusable incontinent product.
Figure 2:
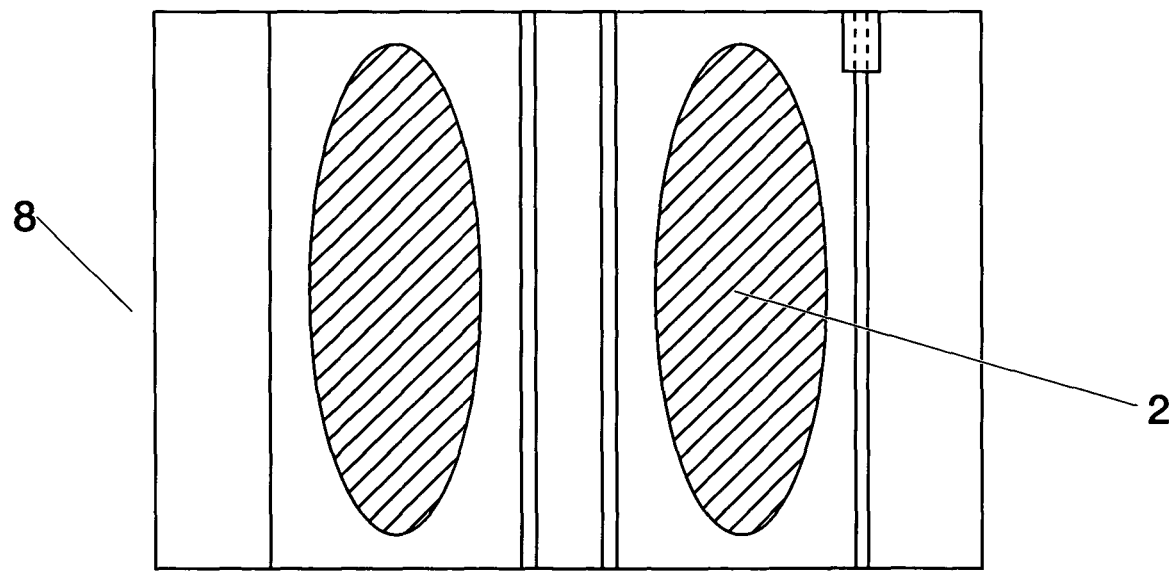
Figure 3:
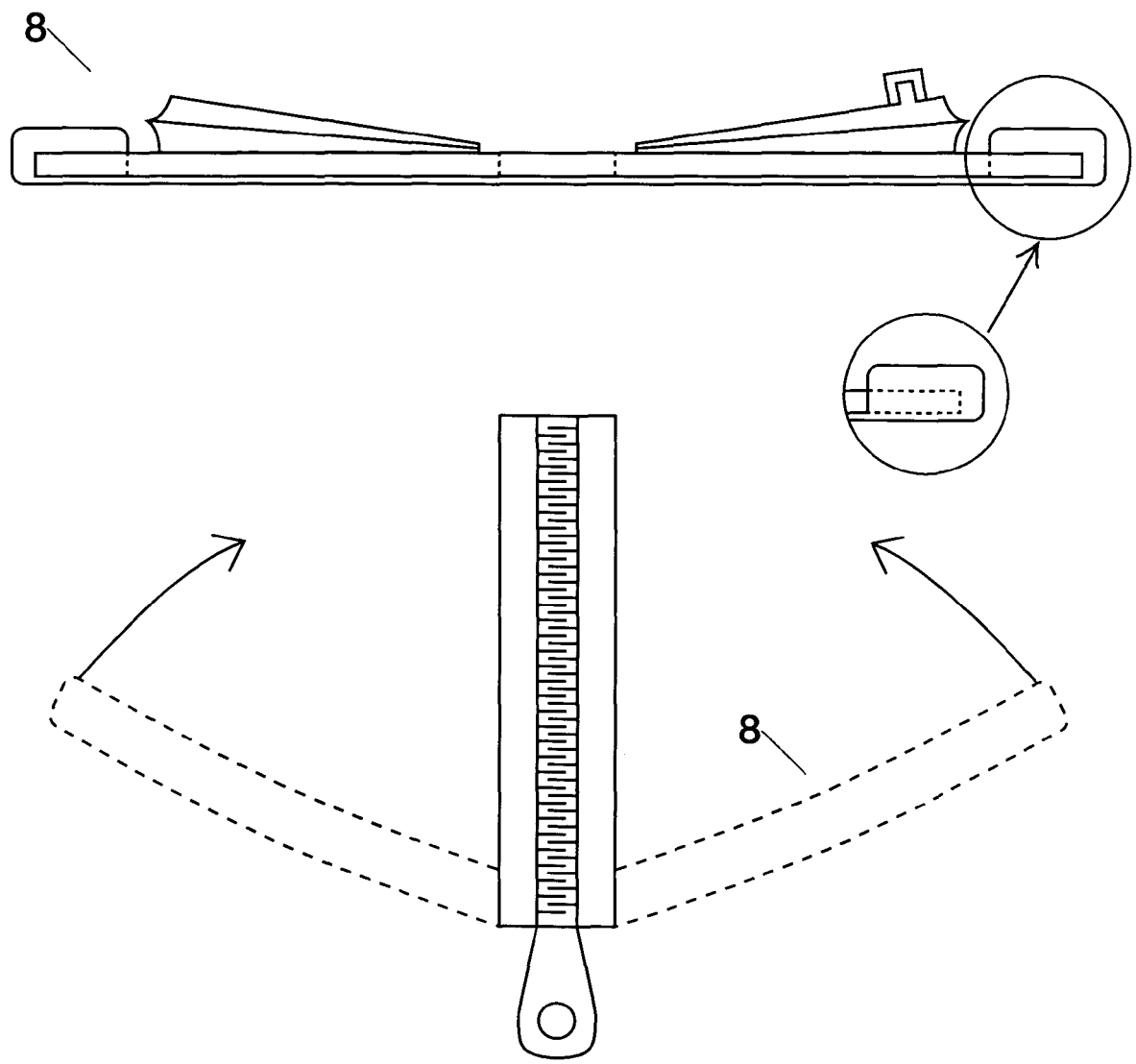
FIG. 3 illustrates an embodiment of the folder having compartments for holding the reusable incontinent product and a zipper for holding the folder closed.

As illustrated in FIGS. 2 and 3, the folder 8 is designed to inconspicuously and conveniently store a number of clean, fresh products 2 as well as products 2 that have been soiled, and which later must be rinsed or washed and dried, before they can be reused. The folder 8 includes by way of example a device made from plastic, leather, cloth, or any other material, or combination of materials, designed specifically to hold both fresh/unused products 2, and products 2 that have been soiled, and are in a wet state.

Additionally, the folder 8 is designed to be carried unobtrusively in any number of places. A woman, for example, may choose to carry the folder in a purse, or sports bag, while a man may choose to carry a folder 8 in the glove box of an automobile, in a golf bag, or in an attaché case, or sports bag.

The folder 8 may be made from many types of materials, and can come in various shapes and sizes. Correspondingly, the following description is only to generally illustrate how the folder 8 might appear and function, and is not necessarily representative of its actual size and design.

The folder 8 may be constructed in two pieces: an exterior cover and a flexible interior, waterproof holder, or "envelope", with both being sized approximately 8"×4½"×2".

The purpose of the exterior cover is to shield, or hide, in an attractive, pleasing manner, the contents of the folder 8, while the interior is designed to contain a supply of both fresh and soiled products 2.

The exterior cover may readily be fabricated from numerous materials, or combinations of materials, such as plastic, leather or cloth, in various designs and colors, and may be constructed by sewing, gluing, thermal, or laser bonding, depending upon the method of assembly chosen and materials used.

The flexible interior may be made of plastic, or any other material that will contain or holds liquids without leakage. Typically, this separate interior piece would contain two compartments. One of the two compartments would hold a supply of fresh (meaning unused) products (represented as a lined, oval shape). The second of the two compartments would hold one or more of the products (represented as a lined, oval shape) after they had been soiled, and would be secured shut by a plastic closure similar to the type found on Ziploc® bags, or a button, or snap, or any other convenient method of sealing to prevent the leakage of liquid.

When ready to be used, the inner waterproof holder is fitted inside the exterior cover by snapping it into place, or slipping under an integral lip built into the cover. With the two pieces now assembled a supply of fresh Products may be inserted into the unit and the folder brought together and closed, or secured, with an ordinary zipper sewn around its periphery, or by buttons, or by hook and loop fasteners, or any other convenient method of joining. The folder 8, now closed and secured, may be is readily carried as previously described.

Later, when an insult has occurred, the folder 8 is opened and the soiled product is temporarily placed in the second compartment, and this compartment closed. A fresh product is removed from the first compartment and positioned next to the skin of the user in the desired location. Thereafter, the folder 8 is again closed and secured as previously shown At the end of any period of time, the soiled products may be removed from the second compartment and rinsed or washed. At the same time, the now empty inner waterproof holder is removed entirely from the outer cover, and also rinsed or washed. When dried, the two pieces are reassembled, and a new supply of fresh products inserted into the first compartment.

This procedure may be repeated as often as needed with the folder thereby providing the incontinent individual with an attractive, convenient, secure, and odor-free method of transporting the products.

The Pant

Figure 4:
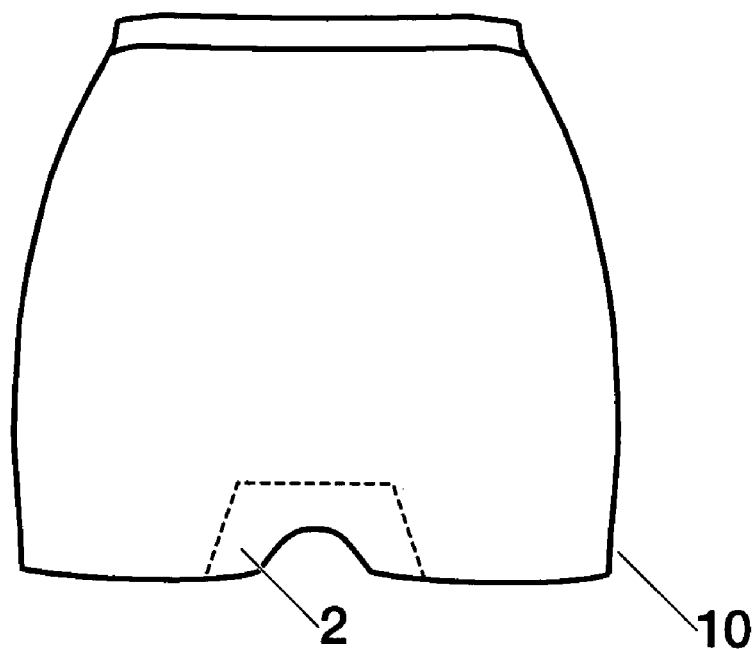
FIG. 4 depicts a pant for holding the reusable incontinent product in place against the skin of a user.

The pant 10, as illustrated in FIG. 4, is operatively configured to hold product 2 in position next to the skin of a user.

By way of example and limitation, the pant 10 may be formed from a lightweight blend of elastic and spandex, or any other suitable fiber, or blend of fibers, the pant 10 (similar to the type manufactured by Tytex, Inc. USA, East Providence, R.I.) is woven on a machine of the kind used in the manufacture of pantyhose for women, but with no legs incorporated into the finished product, making a fine mesh, legless brief. Also contemplated within the present invention are pants 10 having legs or having only partial legs fitting around the thighs of a user. When ready to be used, the pant 10 is pulled on to approximately mid-thigh, and a product 2 placed in position in the area of the crotch. Similarly, the product may be inserted into an opened-ended pouch built into the pant 10. The pant 10 is then pulled up to the waist, now securing the product and holding it in place next to the skin thereby preventing its movement.

When worn by the user in one embodiment, the pant 10 cannot be seen, or observed, through the clothing, such as a skirt, or pair of slacks, for example, by others providing both comfort and security for the user. Equally important, the pant 10 can be readily washed and used numerous times before disposing. The pant 10 may further have the pad 2 permanently attached to the pant 10.

Additionally, because the pant 10 is lightweight, and takes up little room, a spare pant 10 may be easily carried inside the folder 8.

Alternatively, the product 2 may be held in position against the skin with a belt containing straps and clips.

Method of Making the Reusable Incontinent Pad

The term "PEG" means polyethylene glycol, a water soluble, thermoplastic polymer available in varying molecular weights produced by the heterogeneous polymerization of ethylene oxide. Polyethylene glycols demonstrate a low order of toxicity by all routes of exposure, are poorly absorbed from the gastrointestinal tract, nor do they sensitize the skin or irritate the eyes. Polyethylene glycol is classified by the FDA as Codex Grade and is cleared for direct use in numerous pharmaceutical products and most foods.

The term "formulation" means a blend of polyethylene glycol, acid, glyoxal resin, water and other chemicals. The formula compositions are listed on a percent basis of active components and it is understood that solvents such as water can be added to the formulation in varying amounts to have a desired viscosity.

The techniques described in the description below are only illustrative and not meant to imply that there are no other methods or techniques that may be used to make the reusable incontinent product.

Treating the Substrate

First acquiring from a supplier a web, or roll, of a suitable nonwoven substrate made by one of a number of methods such as air laid, spunbond, needlepunched or hydroentangled, the roll is placed at the front of a finishing line using components, such as pads, curing ovens, and other devices, of the type commonly found in most textile finishing facilities.

In the saturation device, a tank holds the formulation which is pumped as needed to the pad. By means of a motors or belts, the nonwoven substrate passes through the pad where it is saturated with the formulation. Pinch rollers may be used to remove excess formulation. Alternatively, the formulation may be sprayed with the excess extracted by a vacuum, or the formulation may be foamed onto, or through, the substrate.

From the pad, the now saturated substrate, carried by pins, or resting on a type of conveyor, passes into the curing oven. The oven has been previously heated to the desired temperature level and as the substrate passes through the interior, the heat causes the fiber hydroxyl groups to react with reactive sites found in the glyoxal resin thereby bonding the fibers and formulation together (cross-linking) and insolubilizing the PEG molecules. A further bonding effect is provided by the formulation reacting with itself. The reaction of the formulation with the fibers, and with itself, results in the formation of a very large molecular network that becomes permanently entangled within the fibers of the nonwoven substrate.

Next, the cured nonwoven substrate passes through a wash box. Here it is washed and agitated in warm water previously treated with soda ash to a pH level of approximately 10.5. This process removes any remaining residual insolubilized chemicals and neutralizes any acids remaining in the substrate to a pH level ranging between 5.5 and 8.8. Additional chemicals, such as softeners, may be added as needed in tanks.

The washed and rinsed substrate now passes into a second drying oven where, by using a combination of pinch rollers and blowing hot air heated with gas or electricity, the moisture picked up during the wash/rinse step is removed, drying the substrate. With the conclusion of this second drying step, the nonwoven material is now a treated substrate. The final step in the process is to wind the treated substrate onto a roll and store until needed for conversion into a finished product.

The benefits of treating a nonwoven substrate with the formulation as described in the steps above, are numerous, and uniquely imbue the treated substrate with permanent attributes, that together, have not heretofore been incorporated into nonwoven structures used in the manufacture of incontinence shields and insert pads, or other types of absorbent products such as underpads, lap pads, wraps, bandages and wound care dressings.

Product Assembly

There are numerous techniques that may be readily used to construct a reusable incontinent product. Gluing, bonding, stamping, slitting, thermal forming, as well as other available methods, are all suitable. Correspondingly the following is only illustrative of the numerous techniques that may be utilized First, a roll of the treated substrate is positioned in front of a device, or machine, of the type typically used to glue, or laminate, two flexible structures together. Beneath this roll, a second roll is positioned containing the barrier. Together, using motors or belts, the treated substrate and barrier now pass over, or under, a series of heated rollers warming the materials to the desired temperatures, thereby causing the surfaces to be joined to become viscous, or sticky. In other instances, a glue, or adhesive may be sprayed across the surface of the treated substrate and/or barrier to provide the bonding or laminating agent.

A third set of rollers now brings the treated substrate and barrier together. depending on the type of bonding agent used, these rolls could be chilled, or at room temperature. By applying pressure to the treated substrate and barrier, the bonding agent, or glue, or adhesive, sets, permanently joining the two structures in a single, integral unit Finally, the joined structure passes through a set of roller dies, with the dies shaped to the desired size and conformation of the product. By squeezing together, the roller dies cut, or press out the product, where it drops to a belt, or other type of carrier. In an embodiment, a wear indicator may be applied to the product before the product is transported to a station for packaging.

Generally using similar methods and techniques to those described herein, to the top surface of the treated substrate a permeable, or perforated, plastic film, or any other material allowing a liquid to pass through, may also be bonded or joined making the product a tri-laminate structure.

Attributes

With the permanent bonding of the formulation to the substrate, the treated substrate acquires the following permanent characteristics:

1. Increased liquid absorption—The polyethylene glycol formulation is hydrophilic and has a natural affinity to liquids, and after the bonding of the formulation to the treated substrate the PEG still maintains its affinity to liquid. Correspondingly, when subjected to an insult, a product will absorb, and retain, many times more liquid (often ten or more times) than the untreated substrate. Equally important, because the fibers in the substrate are now bonded together in a durable matrix structure, the treated substrate may now be rinsed or washed, then dried, and reused numerous times before disposing.

2. Antimicrobial properties—Laboratory testing (using standardized AATCC 100, 147-1993 and ASTM G.21 test methods) has demonstrated that with an effectiveness of 99.9%, treated substrates generally prevent the population of numerous Gram-positive and Gram-negative bacteria providing protection from common odor-causing bacteria such as *B.* and *S. epidermidis*, and harmful bacteria such as *K. peneumoniae* and *P. mirabilis*. The treated substrate is equally effective against certain fungi such as *A. niger* and *A. repens*.

3. Thermal Properties—Treated substrates demonstrate increased thermal capacity (much like ice melts when subjected to heat, or freezes when subjected to cold), compared to a non-treated substrate providing improved comfort for the user. For example, when the skin surface temperature is warm (above a predetermined set point), the released heat is absorbed by the treat substrate thereby cooling the skin surface. Correspondingly, when the skin temperature is cool (below a predetermined set point), the treated substrate releases heat warming the skin surface.

It is believed that this phenomena occurs when the long chain molecules in the polyethylene glycol polymer either contract (absorbing thermal energy), or straighten (releasing thermal energy). This naturally occurring phenomena moderates, or buffers, changes to the ambient surface skin temperature for the wearer, or user, providing a more comfortable product over a wider temperature range (even when wetted after an insult).

4. Durability—Because the fibers of a treated substrate are now bound in a permanent molecular network of resins and PEG entangled within the structure, what was once a nonwoven that when wet would lose its strength, and shred or fall apart, will now, when wetted after an insult, maintain its integrity and hold together. Correspondingly, a product constructed from a treated substrate may now be rinsed, or washed, and reused, numerous times before disposing.

5. Soil Release—A treated substrate demonstrates improved soil release characteristics when compared to an untreated structure giving an improved physical appearance to the product.

It should be understood that the foregoing description is only illustrative of the present invention. Various alternatives and modifications can be devised by those skilled in the art without departing from the spirit of the present invention. Accordingly, the present invention is intended to embrace all such alternatives, modifications and variances that fall within the scope of the claims.

The invention claimed is:

1. An absorbent article comprising:
   a reusable incontinent product including an absorbent layer having a substrate, wherein an insolubilized hydrophilic polyethylene glycol formulation including DMDHEU is bonded and crosslinked to the substrate; and
   a barrier layer operatively aligned with the absorbent layer, wherein the absorbent layer is operatively positioned adjacent to the barrier layer such that the barrier layer prevents a liquid from passing through and out of the absorbent layer and wherein the barrier layer includes a fabric material coated with a polymeric layer.

2. The reusable incontinent product of claim 1, wherein the substrate includes a nonwoven substrate.

3. The reusable incontinent product of claim 1, wherein the substrate exhibits antimicrobial properties.

4. The reusable incontinent product of claim 1, wherein the substrate exhibits a thermal buffering capacity wherein heat is released and stored.

5. The reusable incontinent product of claim 1, wherein the reusable incontinent product further includes a pant.

6. The reusable incontinent product of claim 1, wherein the hydrophilic polyethylene glycol formulation includes on a percent basis of the formulation between about 30% to about 60% polyethylene glycol, between about 10% to about 30% DMDHEU and between about 3% to about 10% of an acid.

7. The reusable incontinent product of claim 1, wherein the polyethylene glycol formulation comprises a polyethylene glycol having a molecular weight between about 1200 and 1500.

8. An absorbent article comprising:
   a reusable incontinent product including an absorbent layer having a substrate, wherein an insolubilized hydrophilic polyethylene glycol formulation including DMDHEU is bonded and crosslinked to the substrate;
   a barrier layer operatively aligned with the absorbent layer, wherein the absorbent layer is operatively positioned adjacent to the barrier layer such that the barrier layer prevents a liquid from passing through and out of the absorbent layer and wherein the barrier layer includes a fabric material coated with a polymeric layer; and
   a wear indicator indicating use comprising a patch that fades as the pad is washed.

* * * * *